United States Patent [19]

Brazdil, Jr.

[11] Patent Number: 6,162,760

[45] Date of Patent: Dec. 19, 2000

[54] ARSENIC PROMOTED VANADIUM-ANTIMONY-OXIDE BASED CATALYST FOR SELECTIVE PARAFFIN AMMOXIDATION

[75] Inventor: James Frank Brazdil, Jr., Highland Heights, Ohio

[73] Assignee: The Standard Oil Company, Chicago, Ill.

[21] Appl. No.: 09/246,266

[22] Filed: Feb. 8, 1999

[51] Int. Cl.[7] ............................. B01J 23/16; C07C 253/00
[52] U.S. Cl. ............................................. 502/353; 558/319
[58] Field of Search ............................... 502/353; 558/319

[56] References Cited

U.S. PATENT DOCUMENTS

| | | | |
|---|---|---|---|
| 4,746,641 | 5/1988 | Guttmann et al. | 502/202 |
| 5,693,587 | 12/1997 | Brazdil, Jr. et al. | 502/353 |
| 5,854,172 | 12/1998 | Brazdil, Jr. et al. | 502/349 |

*Primary Examiner*—Joseph McKane
*Assistant Examiner*—Joseph Murray
*Attorney, Agent, or Firm*—David P. Yusko; Wallace L. Oliver

[57] ABSTRACT

A process of manufacturing acrylonitrile or methacrylonitrile by the catalytic reaction in the vapor phase of a paraffin selected from propane and isobutane with molecular oxygen and ammonia by catalytic contact of the reactants in a reaction zone with a catalyst, the feed composition having a mole ratio of the paraffin to ammonia in the range of from about 2.5 to 16 and a mole ratio of paraffin to oxygen in the range of from about 1.0 to 10, wherein said catalyst has the elements in the proportions indicated by the empirical formula:

$$VSb_mA_aD_bQ_qR_rO_x$$

where
 A is one or more of Ti, Sn, Fe, Cr and Ga;
 D is one or more of Li, Mg, Ca, Sr, Ba, Co, Ni, Zn, Ge, Zr, Cu, Ta, Bi, Ce, In, B and Mn;
 Q is one or more of Mo, W, and Nb;
 R is one or more of As, Te, and Se;
 m equals 0.8 to 4;
 a equals 0.01 to 2;
 d is 0 to 2;
 $0 \leq q < 0.01$; preferably $0 < q < 0.01$, especially $0 < q < 0.005$
 q+r are greater than 0;
 x is determined by the oxidation state of the cations present.

Preferably, the catalyst has been heat treated at a temperature of at least 780° C. and R is selected to be As and Q is selected to be Mo.

21 Claims, No Drawings

ARSENIC PROMOTED VANADIUM-ANTIMONY-OXIDE BASED CATALYST FOR SELECTIVE PARAFFIN AMMOXIDATION

BACKGROUND OF THE INVENTION

Field of the Invention

This invention relates to an improved catalyst for the ammoxidation of propane and isobutane to $\alpha,\beta$-unsaturated mononitriles (acrylonitrile and methacrylonitrile). The preferred application of the invention is in the recycle process in which unreacted propane and isobutane, along with propylene and isobutene produced by the reaction, are recycled back to the reactor for the conversion to acrylonitrile and methacrylonitrile.

Nitriles, such as acrylonitrile and methacrylonitrile, have been industrially produced as important intermediates in the preparation of fibers, synthetic resins, synthetic rubbers and the like. The commercially dominant method for their production requires the ammoxidation of propylene or isobutylene in the presence of ammonia and oxygen at a high temperature in a gas phase in the presence of an ammoxidation catalyst.

However, in view of the price differential between propane and propylene, or the price difference between isobutane and isobutene, recent attention has been drawn to the development of a method and catalyst for the production of acrylonitrile or methacrylonitrile by an ammoxidation reaction wherein the lower alkane such as propane or isobutane is used as a starting material and such lower alkane is catalytically reacted with ammonia and an oxygen-containing gas in the presence of a catalyst.

Earlier attempts to develop an efficient process for the ammoxidation of propane to acrylonitrile produce either insufficient yields or processes that necessitated adding halogen promoters to the feed. The latter procedure would require not only reactors made of special corrosion resistant materials, but also a quantitative recovery of the promoter. This added cost eliminated the advantages of the propane/propylene price differential.

Recent patent publications such as EPO 0767164-A1 and patents such as U.S. Pat. Nos. 5,008,427 and 5,231,214 have been directed to ammoxidation catalyst systems which are directed to solving the problems of previous attempts at propane ammoxidation using specific catalyst. In particular, U.S. Pat. No. 5,008,427 and U.S. Ser. No. 09/048,648 both assigned to the assignees of the present invention are specifically directed to a vanadium-antimony promoted catalyst for propane ammoxidation wherein the catalyst is calcined at temperatures of 780° C. or higher. The catalyst in the present invention and the ammoxidation procedure disclosed herein is directed to an improvement in the '427 patent and copending U.S. Ser. No. 09/048,648.

SUMMARY OF THE INVENTION

It is an object of the present invention to provide an improved process for the ammoxidation of paraffins to unsaturated mononitriles and the corresponding monoolefins.

It is a further object of the present invention to provide an improved catalytic ammoxidation process for making unsaturated mononitriles from lower paraffins without the necessity of using halogen promoters.

It is a still further object in the present invention to provide a process for making a vanadium-antimony promoted oxide catalyst which during calcination, at temperatures of 780° C. or higher, activates the catalyst and minimizes or eliminates clumping together of the catalyst to make larger catalyst particles.

It is another object of the present invention to provide an improved catalyst for use in the ammoxidation of lower paraffins to the corresponding mononitriles and the corresponding monoolefins.

Other objects as well as aspects, features and advantages of the present invention will become apparent from the study of the accompanying disclosure and the claims.

To achieve the foregoing objects and advantages the process of the present invention comprises an $\alpha,\beta$-unsaturated mononitrile, acrylonitrile or methacrylonitrile by the catalytic reaction in the vapor phase of a paraffin selected from propane and isobutane with molecular oxygen and ammonia by catalytic contact of the reactants in a reaction zone with a catalyst, the feed composition having a mole ratio of the paraffin to ammonia in the range of from about 2.5 to 16 and a mole ratio of paraffin to oxygen in the range of from about 1.0 to 10, wherein said catalyst has the elements in the proportions indicated by the empirical formula:

$$VSb_m A_a D_d Q_q R_r O_x$$

where

A is one or more of Ti, Sn, Fe, Cr and Ga;

D is one or more of Li, Mg, Ca, Sr, Ba, Co, Ni, Zn, Ge, Zr, Cu, Ta, Bi, Ce, In, B and Mn;

Q is one or more of Mo, W, Nb, preferably Mo;

R is one or more of As, Te, Se, preferably As; and m equals 0.8 to 4;

a equals 0.01 to 2;

d equals 0 to 2;

$0 \leq q < 0.01$; preferably $0 < q < 0.01$, especially $0 < q < 0.005$ $0 < r < 0.1$; preferably $0 < r < 0.01$ q+r are greater than 0;

x is determined by the oxidation state of the cations present, and the catalyst has been heat treated at a temperature of at least 780° C.

It is another aspect of the present invention to manufacture a promoted vanadium-antimony oxide catalyst which is characterized by being substantially free of clumping by a process comprising heat treating a vanadium-antimony oxide catalyst including at least one or more of the A element and molybdenum at a calcination temperature of at least 780° C. and higher is used.

DETAILED DESCRIPTION OF THE INVENTION

According to one aspect of the invention there is provided a process for making an $\alpha,\beta$-unsaturated mononitrile, acrylonitrile or methacrylonitrile by the catalytic reaction in the vapor phase of a paraffin selected from propane and isobutane with molecular oxygen and ammonia by catalytic contact of the reactants in a reaction zone with a catalyst, the feed composition having a mole ratio of the paraffin to ammonia in the range of from about 2.5 to 16 and a mole ratio of paraffin to oxygen in the range of from about 1.0 to 10, wherein said catalyst has the elements in the proportions indicated by the empirical formula:

$$VSb_mA_aD_dQ_qR_rO_x$$

where

A is one or more of Ti, Sn, Fe, Cr and Ga;

D is one or more of Li, Mg, Ca, Sr, Ba, Co, Ni, Zn, Ge, Zr, Cu, Ta, Bi, Ce, In, B and Mn;

Q is one or more of Mo, W, and Nb, preferably Mo;

R is one or more of As, Te, and Se, preferably As;

m equals 0.8 to 4;

a equals 0.01 to 2;

d is 0 to 2;

$0 \leq q < 0.01$; preferably $0 < q < 0.01$, especially $0 < q < 0.005$ $0 < r < 0.1$; preferably $0 < r < 0.01$ q+r are greater than 0;

x is determined by the oxidation state of the cations present, and the catalyst has been heat treated at a temperature of at least 780° C.

The catalyst of the present invention may be prepared by any method known in the art. Calcination temperatures can be as high as 1200° C. However, calcination temperatures are usually in the range of from about 790° to 1050° C. The calcination temperature can vary from composition to composition but the particular calcination temperature utilized for a given composition can be determined easily by routine experimentation.

In a preferred embodiment of the present invention, the Q and R elements are added to the catalyst after preparation and calcination of the catalyst. For example, the Q and R elements are added to a calcined catalyst comprising V, Sb, A, and D elements. When the R and Q elements are added in this manner, the catalyst may be used after addition of Q and/or R without additional treatment, or the catalyst containing the Q and R element may be furthered calcined at a temperature of up to about 1000° C., preferably below about 650° C., especially preferred being below about 500° C.

In a further preferred embodiment of the present invention, Q is selected to be Mo and R is selected to be As.

Similar to the disclosure in U.S. Pat. No. 5,008,427 and copending U.S. Ser. No. 09/048,648, herein incorporated by reference, it has been found that it is preferable that subscript m in the empirical formula set forth above usually provides the best results when it is at least 1.2 and when it is at most 2.0.

It is also preferred that subscript a as defined above is at least 0.05 and that it preferably does not exceed 0.5 or even 0.4. In a further preferred embodiment element A includes one or more of tin, titanium and iron.

It is particularly important to note that applicant has discovered that catalyst of the present invention containing As or As in combination with Mo produce especially good results. Preferably, the arsenic is present in the catalyst in the range of from greater than zero to about 0.01, more preferred being greater than zero to 0.008, and especially preferred being greater than zero to 0.005. The preferred molybdenum range is from greater than zero to 0.0045, more preferably greater than zero to 0.0035, especially preferred being greater than zero to 0.0030.

Typical reaction conditions for the ammoxidation of the propane or isobutane to acrylonitrile and methacrylonitrile are set forth in U.S. Pat. No. 5,008,427 described above and herein incorporated by reference. The reaction temperature range can vary from 350° to 700° C., but is usually between 430° to 520° C. The average contact time can often be from 0.01 to 10 seconds but is usually between 0.02 to 10 seconds and more, preferably between 0.1 to 5 seconds. The pressure in the reaction zone usually ranges from 2 to 75, but is preferably no more than 50 psia.

In a further preferred embodiment of the present invention, reaction takes place in a fluid bed reactor which is equipped for recycle of the unreacted propane and generated propylene back into the fluid bed reactor.

In order to make the vanadium-antimony oxide catalyst including one or more of the required A elements described in the present invention substantially clump free, the catalyst is calcined at a temperature of 780° C. and higher.

In a further aspect of the present invention, the catalyst comprises a mixed metal oxide promoted $VSbO_x$ characterized by the empirical formula set forth below:

$$VSb_mA_aD_bQ_qR_rO_x$$

where

A is one or more of Ti, Sn, Fe, Cr and Ga;

D is one or more of Li, Mg, Ca, Sr, Ba, Co, Ni, Zn, Ge, Zr, Cu, Ta, Bi, Ce, In, B and Mn;

Q is one or more of Mo, W, and Nb, preferably Mo;

R is one or more of As, Te, and Se, preferably As;

m equals 0.8 to 4;

a equals 0.01 to 2;

d is 0 to 2;

$0 \leq q < 0.01$; preferably $0 < q < 0.01$, especially $0 < q < 0.005$ $0 < r < 0.1$; preferably $0 < r < 0.01$ q+r are greater than 0;

x is determined by the oxidation state of the cations present.

Preferably the catalyst the catalyst has been heat treated at a temperature of at least 780° C.

In a further preferred embodiment of the present invention m equals 1.1 to 1.8; a equals 0.05 to 0.5 and d equals 0 to 0.1.

The examples set forth below are for illustration purposes only and should not be considered as limiting the scope of the invention.

All of the examples were obtained using a fixed bed micro reactor. The catalyst were prepared by adding As, Mo, or As and Mo to a silica supported V/Sb/Sn/Fe/O catalyst prepared by a known conventional catalyst preparation as disclosed in co-pending U.S. Ser. No. 09/048,648 herein incorporated by reference. The elements were added by the incipient wetness procedure using aqueous solutions containing arsenic acid and/or ammonium heptamolybdate. After the catalysts were wetted with the solutions they were dried and calcined at 325° C. for three hours before testing for propane ammoxidation.

TABLE I

| Example | Catalyst | WWH | Feed Ratios C$_3$H$_8$ | NH$_3$ | O$_2$ | N$_2$ | % C$_3$H$_8$ Conv. | % Product Selectivities Acrylonitrile | Useful | Temp °C. Pres (psig) | CO + CO$_2$ |
|---|---|---|---|---|---|---|---|---|---|---|---|
| Example 1 (Comparative) | VSb$_{1.6}$Sn$_{0.05}$Ti$_{0.05}$Fe$_{0.45}$O$_x$ + 20% SiO$_2$ | 2.16 | 3 | 0.8 | 3 | 3 | 20 | 57 | 75 | 480/15 | 25 |
| Example 2 (Invention) | VSb$_{1.6}$Sn$_{0.05}$Ti$_{0.05}$Fe$_{0.45}$As$_{0.004}$O$_x$ + 20% SiO$_2$ | 1.6 | 3 | 0.8 | 2 | 2 | 20 | 57 | 77 | 480/15 | 23 |
| Example 3 (Invention) | VSb$_{1.6}$Sn$_{0.05}$Ti$_{0.05}$Fe$_{0.45}$As$_{0.008}$O$_x$ + 20% SiO$_2$ | 1.57 | 3 | 0.8 | 2 | 2 | 20 | 55 | 78 | 480/15 | 21 |
| Example 4 (Comparative) | VSb$_{1.6}$Sn$_{0.05}$Ti$_{0.05}$Fe$_{0.45}$Mo$_{0.003}$O$_x$ | 1.54 | 3 | 0.8 | 2 | 2 | 20 | 57 | 76 | 480/15 | 24 |
| Example 5 (Invention) | VSb$_{1.6}$Sn$_{0.05}$Ti$_{0.05}$Fe$_{0.45}$As$_{0.004}$Mo$_{0.003}$O$_x$ + 20% SiO$_2$ | 1.53 | 3 | 0.8 | 2 | 2 | 20 | 59 | 80 | 480/15 | 20 |
| Example 6 (Invention) | VSb$_{1.6}$Sn$_{0.05}$Ti$_{0.05}$Fe$_{0.45}$As$_{0.008}$Mo$_{0.003}$O$_x$ + 20% SiO$_2$ | 1.34 | 3 | 0.8 | 2 | 2 | 20 | 56 | 82 | 480/15 | 20 |
| Example 7 (Invention) | VSb$_{1.6}$Sn$_{0.05}$Ti$_{0.05}$Fe$_{0.45}$As$_{0.003}$W$_{0.001}$O$_x$ + 20% SiO$_2$ | 1.20 | 3 | 0.8 | 2 | 2 | 21 | 57 | 78 | 480/15 | 22 |
| Example 8 (Invention) | VSb$_{1.6}$Sn$_{0.05}$Ti$_{0.05}$Fe$_{0.45}$As$_{0.003}$Mo$_{0.002}$O$_x$ + 5% SiO$_2$ | 1.10 | 3 | 0.7 | 1.5 | 3 | 15 | 63 | 84 | 470/23 | 16 |
| Example 9 (Invention) | VSb$_{1.6}$Sn$_{0.05}$Ti$_{0.05}$Fe$_{0.45}$As$_{0.004}$Mo$_{0.001}$O$_x$ + 5% SiO$_2$ | 0.92 | 3 | 0.8 | 2 | 2 | 20 | 62 | 81 | 480/15 | 19 |
| Example 10 (Invention) | VSb$_{1.6}$Sn$_{0.05}$Ti$_{0.05}$Fe$_{0.45}$As$_{0.003}$Mo$_{0.002}$O$_x$ + 5% SiO$_2$ | 0.97 | 3 | 0.8 | 2 | 2 | 21 | 63 | 80 | 480/15 | 20 |
| Example 11 (Invention) | VSb$_{1.6}$Sn$_{0.05}$Ti$_{0.05}$Fe$_{0.45}$As$_{0.003}$Mo$_{0.002}$O$_x$ + 5% SiO$_2$ | 1.03 | 3 | 0.8 | 2 | 2 | 20 | 60 | 81 | 480/15 | 19 |
| Example 12 (Invention) | VSb$_{1.4}$Sn$_{0.2}$Ti$_{0.1}$Fe$_{0.2}$As$_{0.001}$Mo$_{0.001}$O$_x$ | 0.51 | 3 | 0.8 | 2 | 2 | 20 | 61 | 82 | 480/15 | 18 |

1. WWH = weight of propane/wt. of catalyst/hour
2. Useful = (AN) + HCN + acetonitrile + acrylic acid + acrolein + propylene

What I claim as my invention is:

1. A process for making acrylonitrile or methacrylonitrile by the catalytic reaction in the vapor phase of a paraffin selected from propane and isobutane with molecular oxygen and ammonia by catalytic contact of the reactants in a reaction zone with a catalyst, the feed composition having a mole ratio of the paraffin to ammonia in the range of from about 2.5 to 16 and a mole ratio of paraffin to oxygen in the range of from about 1.0 to 10, wherein said catalyst is characterized by the following empirical formula:

$$VSb_mA_aD_bQ_qR_rO_x$$

where
   A is one or more of Ti, Sn, Fe, Cr and Ga;
   D is one or more of Li, Mg, Ca, Sr, Ba, Co, Ni, Zn, Ge, Zr, Cu, Ta, Bi, Ce, In, B and Mn;
   Q is one or more of Mo, W, and Nb;
   R is As;
   m equals 0.8 to 4;
   a equals 0.01 to 2;
   d is 0 to 2;
   $0 \leq q < 0.01$;
   $0 < r < 0.1$;
   q+r are greater than 0;
   x is determined by the oxidation state of the cations present, and the catalyst has been heat treated at a temperature of at least 780° C.

2. The process of claim 1 wherein m ranges from about 1.2 to 2.0.

3. The process of claim 1 wherein a ranges from about 0.05 to 0.5.

4. The process of claim 1 wherein a ranges from about 0.05 to 0.4.

5. The process of claim 1 wherein A includes one or more of tin, titanium and iron.

6. The process of claim 1 wherein the reaction takes place in a fluid bed reactor.

7. The process of claim 6 wherein any unreacted propane or isobutane is recycled into the fluid bed reactor.

8. The process of claim 1 wherein q is greater than zero.

9. The process of claim 8 wherein Q is selected to be Mo.

10. The process of claim 8 wherein r ranges from greater than zero to about 0.0030.

11. The process of claim 10 wherein r ranges from greater than zero to about 0.0030.

12. The process of claim 8 wherein r ranges from greater than zero to about 0.006.

13. The process of claim 1 wherein r ranges from greater than zero to about 0.006.

14. A process for the manufacture of a substantially clump free promoted vanadium-antimony oxide catalyst having the empirical formula $$VSb_mA_aD_bQ_qR_rO_x$$

where
   A is one or more of Ti, Sn, Fe, Cr and Ga;
   D is one or more of Li, Mg, Ca, Sr, Ba, Co, Ni, Zn, Ge, Zr, Cu, Ta, Bi, Ce, In, B and Mn;
   Q is one or more of Mo, W, and Nb;
   R is one or more of As, Te, and Se;
   m equals 0.8 to 4;
   a equals 0.01 to 2;
   d is 0 to 2;
   $0 \leq q < 0.01$;
   $0 < r < 0.1$;
   q+r are greater than 0;
   x is determined by the oxidation state of the cations present, and
   the catalyst has been heat treated at a temperature of at least 780° C.;

comprising incorporating one or more of the required A elements in the catalyst along with at least As prior to the calcination of the catalyst, and calcining the catalyst including the A element and As at a temperature of at least 780° C.

15. The process of claim 14 wherein the arsenic is added to the catalyst after the catalyst has been calcined at a temperature of at least 780° C.

16. The process of claim 14 wherein the arsenic is added to the catalyst by uniformly wetting the calcined catalyst with an aqueous solution containing arsenic, drying the catalyst and heat treating the catalyst.

17. The process of claim 14 wherein the arsenic is added to the catalyst by impregnating said catalyst with a powder comprising an arsenic containing material.

18. The process of claim 17 wherein the powder is selected from the group consisting of Arsenic acid, $As_2O_3$ and $As_2O_5$.

19. A catalyst useful in the ammoxidation of propane and isobutane to acrylonitrile and methacrylonitrile respectively comprising a promoted mixed metal oxide VSbOx catalyst characterized as having the following empirical formula $$VSb_m A_a D_b Q_q R_r O_x$$

where

A is one or more of Ti, Sn, Fe, Cr and Ga;

D is one or more of Li, Mg, Ca, Sr, Ba, Co, Ni, Zn, Ge, Zr, Cu, Ta, Bi, Ce, In, B and Mn;

Q is one or more of Mo, W, and Nb;

R is As;

m equals 0.8 to 4;

a equals 0.01 to 2;

d is 0 to 2;

$0 \leq q < 0.01$;

$0 < r < 0.1$;

q+r are greater than 0;

x is determined by the oxidation state of the cations present.

20. The catalyst of claim 19 wherein q is greater than zero.

21. The catalyst of claim 20 wherein Q equals Mo.

* * * * *

UNITED STATES PATENT AND TRADEMARK OFFICE
CERTIFICATE OF CORRECTION

| | | |
|---|---|---|
| PATENT | : | 6,162,760 |
| DATED | : | December 19, 2000 |
| INVENTOR(S) | : | James frank Brazdil, Jr. |

It is certified that error appears in the above-identified patent and that said Letters Patent is hereby corrected as shown below:

<u>Col.</u>  <u>Line</u>

6   39   "process of claim 10"

should read:
"process of claim 1"

Signed and Sealed this

Fifteenth Day of May, 2001

Attest:

NICHOLAS P. GODICI

Attesting Officer    Acting Director of the United States Patent and Trademark Office